United States Patent [19]

Neville et al.

[11] 4,150,143

[45] Apr. 17, 1979

[54] N-SUBSTITUTED-ACYLAMINO-OXAZOLES AS ANTIASTHMA AGENTS

[75] Inventors: Martin C. Neville, Tadley; John P. Verge, Henley-on-Thames, both of England

[73] Assignee: Lilly Industries Limited, London, England

[21] Appl. No.: 779,891

[22] Filed: Mar. 21, 1977

Related U.S. Application Data

[63] Continuation of Ser. No. 533,417, Dec. 16, 1974, abandoned.

[30] Foreign Application Priority Data

Dec. 17, 1973 [GB] United Kingdom ............... 58351/73

[51] Int. Cl.$^2$ .................. C07D 263/48; A61K 31/42
[52] U.S. Cl. ................................ 424/272; 260/307 R; 542/414; 542/421; 542/426; 546/209
[58] Field of Search .................... 260/307 R; 424/272; 542/321

[56] References Cited

U.S. PATENT DOCUMENTS

| 3,152,136 | 10/1964 | Harris et al. ......................... 260/295 |
| 3,682,945 | 8/1972 | Engelhart ...................... 260/306.8 F |

FOREIGN PATENT DOCUMENTS

| 2459380 | 6/1975 | Fed. Rep. of Germany. |
| 1264258 | 2/1972 | United Kingdom. |
| 1290841 | 9/1972 | United Kingdom. |

OTHER PUBLICATIONS

Fromm et al, C.A. 23, 2177, (1929).
Beyer et al, C.A. 65, 8892g, (1966).
Clerin et al, Bull. de la Soc. Chim. Fr., 3127–41, (1973).

*Primary Examiner*—Raymond V. Rush
*Attorney, Agent, or Firm*—Charles W. Ashbrook; Walter E. Buting; Everet F. Smith

[57] ABSTRACT

Oxazoles which are substituted in the 2,4 or 5-position with an N-substituted-acylamino group have anti-allergic activity. Methods of making such compounds, pharmaceutical compositions containing the active compounds of the invention and methods of treating asthma utilizing such compounds are provided.

9 Claims, No Drawings

N-SUBSTITUTED-ACYLAMINO-OXAZOLES AS ANTIASTHMA AGENTS

This is a continuation of application Ser. No. 533,417, filed Dec. 16, 1974, now abandoned.

This invention relates to heterocyclic chemical compounds and more particularly to certain novel oxazole derivatives which possess pharmacological activity and/or are useful as intermediates in preparing such active compounds. The invention also includes processes for preparing the compounds of the invention. Furthermore the invention includes within its scope pharmaceutical compositions containing the pharmacologically active compounds and methods of treatment of animals, including humans, comprising administering thereto an effective dose of the compound or compounds or of pharmaceutical compositions comprising the active compound or compounds.

According to the present invention there are provided novel oxazole derivatives of the formula:

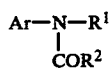

wherein Ar represents an optionally substituted oxazole group, the acylamino group $-NR^1COR^2$ being attached at the 2,4 or 5- position thereof, $R^1$ is $C_{1-6}$ alkyl, $C_{2-6}$ alkenyl, $C_{3-6}$ alkenyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, optionally substituted phenyl-$C_{1-6}$ alkyl or optionally substituted phenyl-$C_{2-6}$ alkenyl; and $R^2$ is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, optionally substituted phenyl, optionally substituted phenyl-$C_{1-6}$ alkyl or optionally substituted phenyl-$C_{2-6}$ alkenyl; or $R^1$ and $R^2$ together form a lactam ring having 5 to 7 ring atoms.

The oxazole nucleus may be substituted in one or both available positions by a group selected from formyl, carboxyl, hydroxy, $C_{1-4}$ hydroxyalkyl, $C_{1-4}$ alkyl, $C_{3-10}$ cycloalkyl, $C_{3-6}$ acyloxyalkyl or an optionally substituted phenyl group. The available positions in the oxazole ring are the two carbon atoms not substituted by the acylamino group.

Compounds in which the acylamino group $-NR^1COR^2$ is attached to the 2- position of the oxazole nucleus are preferred from the point of view of ease of preparation.

A particularly preferred class of compounds according to the present invention are those of formula:

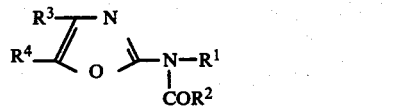

wherein $R^1$ is $C_{1-6}$ alkyl, $C_{2-6}$ alkenyl, $C_{2-6}$ alkoxyalkyl, $C_{3-8}$ cycloalkyl, $C_{3-8}$ cycloalkyl-$C_{1-6}$ alkyl, optionally substituted phenyl-$C_{1-6}$ alkyl or optionally substituted phenyl-$C_{2-6}$ alkenyl; $R^2$ is $C_{1-6}$ alkyl, $C_{1-6}$ haloalkyl, $C_{3-6}$ alkenyl, $C_{3-8}$ cycloalkyl, $C_{3-8}$ cycloalkyl-$C_{1-6}$ alkyl, optionally substituted phenyl, optionally substituted phenyl-$C_{1-6}$ alkyl or optionally substituted phenyl-$C_{3-6}$ alkenyl, or $R^1$ and $R^2$ together form a lactam ring having 5 or 6 ring atoms, and wherein $R^3$ and $R^4$ are independently hydrogen, $C_{1-4}$ alkyl, $C_{1-4}$ hydroxyalkyl, $C_{3-8}$ cycloalkyl, $C_{3-6}$ acyloxyalkyl or an optionally substituted phenyl group.

The term "$C_{1-6}$ alkyl" as used herein means a straight or branched chain alkyl group containing from 1 to 6 carbon atoms such as methyl, ethyl, isopropyl, n-butyl, s-butyl, isobutyl, t-butyl, n-amyl, s-amyl, n-hexyl, 2-ethylbutyl or 4-methylamyl.

Similarly the term "$C_{1-4}$ alkyl" as used herein means a straight or branched chain alkyl group containing from 1 to 4 carbon atoms, namely methyl, ethyl, isopropyl, n-propyl, n-butyl, isobutyl, s-butyl, t-butyl. "$C_{1-4}$ hydroxyalkyl" and "$C_{3-6}$ acyloxyalkyl" mean the aforementioned $C_{1-4}$ alkyl groups substituted with an hydroxy group and acyloxy group respectively. "$C_{2-6}$ alkoxyalkyl" and "$C_{1-6}$ haloalkyl" mean the aforementioned $C_{1-6}$ alkyl groups substituted with an alkoxy group or one or more halogen atoms, such as methoxyethyl, ethoxyethyl, ethoxybutyl, dibromoethyl, trifluoromethyl, 1-chloroethyl, 1,1-dichloroethyl, 1-iodobutyl or pentafluoroethyl.

The terms "$C_{2-6}$ alkynyl" and "$C_{3-6}$ alkynyl" are used herein to indicate alicyclic hydrocarbon groups having 2 to 6 and 3 to 6 carbon atoms which contain a -C≡C- group. However, it should be noted that the -C≡C- group cannot be directly adjacent to the nitrogen atom of the acylamino group.

"$C_{3-10}$ cycloalkyl" means a saturated ring having from 3 to 10 carbon atoms in the ring such as cyclopropyl, cyclobutyl, cyclopentyl, cyclooctyl, or adamantyl. "$C_{3-10}$ cycloalkyl-$C_{1-6}$ alkyl" means the aforementioned saturated rings substituted with the aforementioned $C_{1-6}$ alkyl groups at any available position.

The term "optionally substituted phenyl" as used herein means a phenyl group unsubstituted or substituted by one or more groups which do not substantially alter the pharmacological activity of the compounds of formula I, such as halogen, trifluoromethyl, methyl, methoxy, or nitro groups.

The term "carboxyalkyl" as used herein means a $C_{1-5}$ alkyl group substituted by a carboxylic acid group. Examples of such groups are carboxymethyl, carboxyethyl, carboxypropyl and carboxybutyl.

Preferred classes of compounds falling within the scope of the oxazoles defined in formula I or II above are those having one or more of the following characteristics:

(a) $R^1$ is $C_{3-6}$ alkyl, for instance n-butyl and n-propyl,
(b) $R^1$ is $C_{3-4}$ alkenyl,
(c) $R^1$ is phenyl-$C_{1-2}$ alkyl,
(d) $R^2$ is phenyl,
(e) $R^2$ is $C_{1-4}$ alkyl, for instance methyl, n-propyl and i-propyl,
(f) $R^2$ is $C_{3-5}$ cycloalkyl,
(g) $R^1$ and $R^2$ taken together form a lactam ring having 5 carbon atoms,
(h) one or both of the available positions in the oxazole nucleus is substituted by a methyl group,
(i) one or both of the available positions in the oxazole nucleus is substituted by a hydroxymethyl group,
(j) the oxazole nucleus, not considering the acylamino group, is unsubstituted.

The present invention also provides a process for preparing the novel oxazole derivative of formula I or II which process comprises
  (a) acylating,
    (i) a compound of formula III:

$$ArNHR^1 \qquad \qquad III$$

where Ar and $R^1$ are as defined above, or
(ii) a compound of formula Ar $NH_2$ with an ω-haloacyl halide and cyclising the resultant ω-haloacylamino oxazole to form a compound of formula I or II in which $R^1$ and $R^2$ together form a lactam ring having 5 to 7 carbon atoms;

(b) alkylating a compound of formula IV:

$$\underset{\underset{COR^2}{|}}{Ar-N-H} \qquad IV$$

where Ar and $R^2$ are as defined above.

Thus, for example, 2-(N-butyl-isobutyramido)-4-methyloxazole can be prepared by acylating 2-butylamino-4-methyloxazole or by alkylating 2-isobutyramido-4-methyloxazole.

It will of course be appreciated that, when the oxazole nucleus is substituted by hydroxyalkyl in the above compound of formula III, the resultant acylation to a compound of formula IV will also usually result in the conversion of the hydroxyalkyl substituent to an acyloxyalkyl substituent. The latter however may readily be selectively hydrolysed back to the desired hydroxyalkyl substituent.

The majority of the compounds of formula III and IV, are novel but some are known compounds, see for example YAKUGAKU ZASSHI 91, 425, (1971); 91 436 (1971), Annalen 596, 117, (1955) and Chem. Ber. 1928 (1959).

Compounds of formula III, in which the acylamino group is at the 2- position of the oxazole nucleus, may be prepared by the condensation of an α-hydroxy or α-acyloxy ketone or aldehyde having the following formulae respectively:

$$\underset{\underset{OH}{|}}{R^4-CH-COR^3} \qquad V$$

$$\underset{\underset{O\ Acyl}{|}}{R^4-CH-COR^3} \qquad VI$$

$R^3$ and $R^4$ being as defined above, with cyanamide or a mono-substituted cyanamide having the formula:

$$R^1NH\text{-}CN \qquad VII$$

wherein $R^1$ is as defined above.

Alternatively, any similar compound V or VI may be used having an appropriate leaving group instead of the acyl group.

This condensation may be carried out in the presence of an acid or a basic catalyst (the latter being much preferred) in a suitable solvent, for example aqueous dioxan. A preferred acid catalyst is aqueous HCl and a preferred basic catalyst is aqueous NaOH. The condensation and cyclisation reaction provides the intermediate 2-substituted-amino oxazole of formula III.

Cyanamide and its lower alkyl derivatives, i.e. the methyl and ethyl derivatives are known (see J. Org. Chem. 38, 1325, (1973)). Other cyanamides are novel and can be prepared by reacting a compound of formula $R^1NH_2$, where $R^1$ is as above defined, with cyanogen bromide. It should be noted that, in general, cyanamides are unstable and, accordingly, should be used immediately after preparation or, if stored, should be stabilised with acetic acid or cyanogen bromide.

The acylation of the compound of formula III may be carried out with an acid halide having the formula $R^2CO$-X wherein X is chlorine or bromine and $R^2$ is as defined above in the presence of a proton acceptor, such as pyridine or triethylamine, in an inert solvent, such as benzene.

The acylation may also be carried out by heating the amino oxazole of formula III with a suitable acid anhydride, $(R^2CO)_2O$, in an inert solvent.

Those skilled in the art will immediately appreciate that a wide variety of other acylating conditions can be used (see, for example, "The Chemistry of Amides" 1971 by A. J. Beckwith; "Survey of Organic Synthesis", 1970 by Buehler and Pearson; "Organic Functional Group Preparations" 1968 by Sandler and Karo; "Reagents for Organic Synthesis" 1968 by Fieser and Fieser, etc.).

When it is desired that $R^1$ and $R^2$ should form a lactam ring, an amino oxazole, having the formula $ArNH_2$, is acylated with an ω-halo acyl halide and the resulting haloacylamino oxazole is cyclised in the presence of a powerful proton acceptor such as DBN (1:5 diazabicyclo[4,3,0]non-5-ene).

Compounds of formula IV can be alkylated by dissolving the amide in a suitable inert, anhydrous, polar solvent such as dimethylformamide, forming an alkali metal salt thereof with an alkali metal hydride, preferably sodium hydride, and then treating the salt with an alkylating agent of formula $R^1X^1$ where $X^1$ is a reactive atom such as a halogen atom or a reactive group such as an alkyl sulphate group. Alternatively, the abovementioned hydride canbe replaced by an appropriate anhydrous alkali metal carbonate such as potassium or sodium carbonate in an inert solvent such as methyl ethyl ketone or dimethylformamide. In the latter case, the reaction mixture is preferably heated to accomplish the alkylation. Of course, alkylating agents and alkylating reaction conditions other than those specified above can be utilised, the nature of these being readily apparent to those acquainted with the art.

It should be noted that for the preparation of compounds of formula I in which the acylamino group is at the 4- position of the oxazole ring, preparative difficulties may be encountered unless a compound of formula III is first acylated and the product IV then alkylated. In other words, for 4-acylamino oxazoles of formula I, it is highly desirable that acylation should proceed alkylation.

It will be understood the scope of the invention extends not only to an overall process for preparing the novel compounds of the invention as described hereinbefore but also to the individual synthetic steps as herein described, and combinations of two or more of such synthetic steps.

For the most part the intermediates of formula V and of formula VI above are either known compounds or may be prepared by known methods, (see, for example, Ind. Eng. Chem. 39, 55, (1949) and Org. Synth. Coll. Vol. II, p.5). A new and preferred method, however, for preparing compounds of formula VI is that described in the specification of Roger Garrick Harrison's U.S. Pat. Application Ser. No. 533,358, now U.S. Pat. No. 3,965,157 filed this even date herewith, which method involves the addition of the aldehyde $R^4CHO$ to a 2-lithio-2-$R^3$ substituted-1,3-dithiane followed by acylation and removal of the dithioacetal moiety by mercuric ion assisted hydrolysis as illustrated in the following reaction scheme:

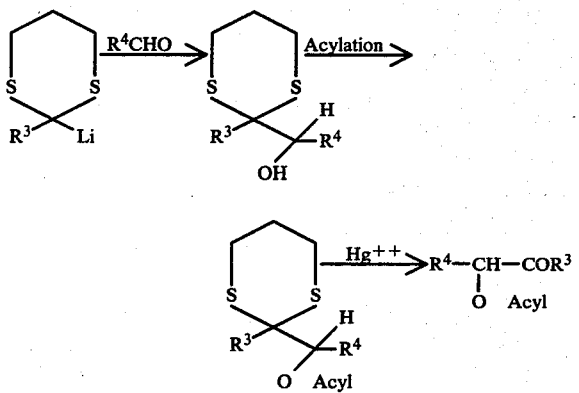

As mentioned above, many intermediates of formula III and IV are novel compounds. Such novel compounds can be represented by the general formula VIII:

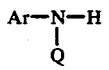   VIII wherein Ar is as previously defined, and Q is the group $R^1$ or $-COR^2$ provided that
(a) when Q is $-COR^2$ and the -NHQ group is attached to the 2- position of the oxazole nucleus, $R^2$ cannot be $C_{2-6}$ alkyl, when
   (i) one of the 4- and 5- positions of the oxazole nucleus is unsubstituted, the other being substituted by a $C_{1-4}$ alkyl group;
   (ii) both of the 4- and 5- positions of the oxazole nucleus are substituted by a $C_{1-4}$ alkyl group; or
   (iii) the oxazole nucleus is unsubstituted;
(b) when Q is $-COR^2$ and the NHQ group is attached to the 2- position of the oxazole nucleus, $R^2$ cannot be methyl or unsubstituted phenyl;
(c) when Q is $R^1$, the other two positions in the oxazole nucleus not occupied by the $-NHR^1$ group cannot both be occupied by unsubstituted phenyl groups;
(d) when Q is $R^1$, and the $-NHR^1$ group is at the 2- position of the oxazole nucleus, $R^1$ cannot be ethyl when the 4 and 5- positions in the oxazole ring are both substituted by methyl.

A preferred class of amine intermediates of formula VIII are those of formula (IX):

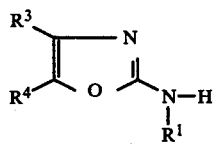   IX where $R^3$ and $R^4$ are independently hydrogen, $C_{1-4}$ alkyl or $C_{1-4}$ hydroxyalkyl and wherein $R^1$ is $C_{3-6}$ alkyl.

Compounds of formula I and II have been shown to be useful in the prophylactic and therapeutic treatment of immediate hypersensitivity diseases including asthma and in the alleviation of *status asthmaticus*. In certain cases the compounds have been found to be useful in diseases in which excessive amounts of prostaglandins are released and as a respiratory stimulant. The compounds have low toxicity.

The compounds of compositions of the present invention may be administered by various routes and for this purpose may be formulated in a variety of forms. Thus the compounds or compositions may be administered by the oral and rectal routes, topically, parenterally, e.g. by injection and the continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing form 5 to 500 mg. (from 5.0 to 50 mg. in the case of parental administration, from 5.0 to 50 mg. in the case of inhalation and from 25 to 500 mg. in the case of oral or rectal administration) of a compound of formula I. Dosages of from 0.5 to 300 mg/kg per day, preferably 0.5 to 20 mg/kg of active ingredient may be administered although it will, of course, readily be understood that the amount of the compound or compounds of formula I or II actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for single therapeutic administration.

The formulations of the present invention normally will consist of at least one compound of formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material, which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidine, cetostearyl alcohol, starch, modified starches, gum acacia, calcium phosphate, cocoa butter, ethoxylated esters, oil of theobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminum, magnesium or calcium stearates, talc or mineral oil.

Examples of the novel compounds of the invention are:

2-(N-butylacetamido)-4-methyl oxazole
2-(N-butylpropionamido)-4-methyl oxazole
2-(N-butylbutyramido)-4-methyl oxazole
2-(N-butylpentanamido)-4-methyl oxazole
2-(N-butylhexanamido)-4-methyl oxazole
2-(N-butylisobutyramido)-4-methyl oxazole
2-(N-butyl-2-ethylbutyramido)-4-methyl oxazole
2-(N-butylpivalamido)-4-methyl oxazole
2-(N-butylcyclopropanecarboxamido)-4-methyl oxazole
2-(N-butylcyclobutanecarboxamido)-4-methyl oxazole
2-(N-butylcclopentanecarboxamido)-4-methyl oxazole
2-(N-butylcyclohexanecarboxamido)-4-methyl oxazole
2-(N-butylcycloheptanecarboxamido)-4-methyl oxazole
2-(N-butylphenylacetamido)-4-methyl oxazole
2-(N-butylphenylpropionamido)-4-methyl oxàzole
2-(N-butylbenzamido)-4-methyl oxazole
2-(N-butyl-2-chlorobenzamido)-4-methyl oxazole
2-(N-butyl-3-chlorobenzamido)-4-methyl oxazole
2-(N-butyl-4-chlorobenzamido)-4-methyl oxazole
2-(N-butyl-2-methoxybenzamido)-4-methyl oxazole
2-(N-butyl-4-methoxybenzamido)-4-methyl oxazole
2-(N-butyl-4-toluamido)-4-methyl oxazole
2-(N-butyl-3-trifluoromethylbenzamido)-4-methyl oxazole
2-(N-butyl-4-nitrobenzamido)-4-methyl oxazole
2-(N-methylacetamido)-4-methyl oxazole
2-(N-methylisobutyramido)-4-methyl oxazole
2-(N,2-diethylbutyramido)-4-methyl oxazole
2-(N-isopropylacetamido)-4-methyl oxazole
2-(N-isopropylpropionamido)-4-methyl oxazole
2-(N-isopropylbutyramido)-4-methyl oxazole
2-(N-isopropylisobutyramido)-4-methyl oxazole
2-(N-s-butylacetamido)-4-methyl oxazole
2-(N-s-butylpropionamido)-4-methyl oxazole
2-(N-s-butylbutyramido)-4-methyl oxazole
2-(N-s-butylisobutyramido)-4-methyl oxazole
2-(N-hexylacetamido)-4-methyl oxazole
2-(N-hexylisobutyramido)-4-methyl oxazole
2-(N-benzylacetamido)-4-methyl oxazole
2-(N-benzylpropionamido)-4-methyl oxazole
2-(N-benzylbutyramido)-4-methyl oxazole
2-(N-benzylisobutyramido)-4-methyl oxazole
2-(N-n-propylpentamido)-4-methyl oxazole
2-(N-[2-methoxyethyl]acetamido)-4-methyl oxazole
2-(N-[2-methoxyethyl]propionamido)-4-methyl oxazole
2-(N-[2-methoxyethyl]butyramido)-4-methyl oxazole
2-(N-[2-methoxyethyl]2-ethylbutyramido)-4-methyl oxazole
2-(N-[2-methoxyethyl]isobutyramido)-4-methyl oxazole
2-(N-allylacetamido)-4-methyl oxazole
2-(N-allylpropionamido)-4-methyl oxazole
2-(N-allylbenzamido)-4-methyl oxazole
2-(N-allylbutyramido)-4-methyl oxazole
2-(N-allyl-2-ethylbutyramido)-4-methyl oxazole
2-(N-butyldibromoacetamido)-4-methyl oxazole
2-(N-ethylacetamido)-4-methyl oxazole
2-(N-ethylbutyramido)-4-methyl oxazole
2-(N-ethylacetamido)-4,5-dimethyl oxazole
2-(N-ethylpropionamido)-4,5-dimethyl oxazole
2-(N-ethylbutyramido-4,5-dimethyl oxazole p0 2-(N-ethylisobutyramido)-4,5-dimethyl oxazole
2-(N-butylacetamido)-4,5-dimethyl oxazole
2-(N-butylisobutyramido)-4,5-dimethyl oxazole
2-(N-butylpropionamido)-4,5-dimethyl oxazole
2-(N-butylisobutyramido) oxazole
2-(N-butylisobutyramido)-4-isopropyl oxazole
2-(N-butylisobutyramido)-4-cyclohexyl oxazole
2-(N-butylisobutyramido)-4-phenyl oxazole
2-(N-butylisobutyramido)-4-butyl oxazole
1-(4-methyloxazol-2-yl)-2-pyrrolidone
2-(N-allylisobutyramido)-4-methyl oxazole
2-(N-cinnamylisobutyramido)-4-methyl oxazole
2-(N-crotylisobutyramido)-4-methyl oxazole
2-(N-dimethylallylisobutyramido)-4-methyl oxazole
2-(N-butylcinnamamido)-4-methyl oxazole
2-(N-butylcinnamamido)-4-methyl oxazole
2-(N-butylacrylamido)-4-methyl oxazole
2-(N-butyldimethylacrylamido)-4-methyl oxazole
2-(N-butylcrotonamido)-4-methyl oxazole The following Examples will further illustrate the preparation of novel compounds of the invention. Where reference is made in the following Examples to a boiling point as being the air-bath temperature, this means that the compounds in question were distilled in a Kugelrohr distillation apparatus and the temperature quoted was that of the air-bath surrounding the distillation flask during distillation of the product.

EXAMPLE 1

(a) n-Butylcyanamide BrCN + n-BuNH₂ → n-BuNHCN

Cyanogen bromide (94.6g., 0.88 m) in dry ether (200 c.c.) was stirred with anhydrous sodium carbonate (200 g., 1.88m), and maintained at −20° to −10° C. during the addition of n-butylamine (88 g., 0.88 m) over 1 hour. Stirring was continued for a further hour as the temperature rose to 0° C. The mixture was then filtered and evaporated to leave a colourless oil, 84 g., 96%.

A sample of the above (50 g.) was distilled at 100° C./2 mm. as a colourless mobile liquid, which rapidly polymerised unless stabilised as described below.

Since alkylcyanamides tend to be unstable, one percent by weight of cyanogen bromide was added to the cyanamide product of the reaction. In the presence of this stabilising agent, the n-butylcyanamide prepared by the above reaction could be stored at room temperature with no, or only slight, decomposition.

When subsequent reactions were to be conducted in aqueous media, the cyanamide was prepared in a suitable water-miscible solvent (preferably THF) and the isolation procedure omitted.

(b) (i) 2-Butylamino-4-methyloxazole

Base catalysed procedure

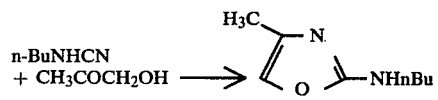

n-Butylcyanamide (13 g., 0.13 m.) and hydroxyacetone (9.7 g., 0.13 m.) in dioxan (25 cc.) were stirred during the dropwise addition of 2N sodium hydroxide solution (70 c.c., 0.15 m.). The temperature rose spontaneously to 35° C. After the addition was complete, stirring was continued at room temperature for a further 2 hours.

Water (100 c.c.) was then added and the product isolated in ether.

The ether extract was washed with saturated brine, dried, and evaporated to leave a pale yellow oil.

Distillation gave a colorless oil b.p. 80° C./0.5 mm., 14.6 g., 73%.

(ii) Acid catalysed procedure

Hydroxyacetone (2.25 g., 0.03 gave a in cold (10° C.), concentrated hydrochloric acid (2.75 c.c.) was treated with butylcyanamide (3 g., 0.03 m.). After the addition, (5 minutes) the cooling bath was removed and the temperature allowed to rise to 40° C. After a further 1 hour, the solution was poured into cold 5 N NaOH (50 c.c.) and the product isolated by extraction in ether. The extract was washed in brine, dried, and evaporated leaving a yellow oil, 3.5 g. Distillation a colourless product, 2.6 g., 56%, which was identical with the product obtained in Example 1 (b) (i).

(iii) One-pot procedure

Cyanogen bromide (1457 g., 13.75 mol.) was dissolved in dry T.H.F. (7 l.) and anhydrous sodium carbonate (2914 g., 27.5 mol.) was added. The mixture was cooled to below −10° C. and n-butylamine (1 kg., 13.67mol) was added slowly over 1 hour with vigorous stirring, maintaining the temperature below −10° C. After the addition, the mixture was stirred for a further 30 minutes at −10° C. then allowed to warm to +10° C. and filtered.

The solids were washed with THF (500 ml.) and the combined filtrates were diluted with water (7 l.) and 54% w/w aqueous acetol (2.8 kg., 20.41 mol.) was added. This was stirred vigorously under $N_2$ during the addition of 50% aqueous sodium hydroxide (500 ml.) over 15 minutes. After the addition, the mixture was stirred for a further 1½ hours at room temperature and then extracted with ether (4 × 2½ l.). The combined extracts were washed with water, dried over magnesium sulphate and evaporated in vacuo. The resulting oil was distilled under vacuum to give the amine 1705 g. (81%) b.p. 92–94° C./1 mm., as a pale yellow oil.

EXAMPLES 2 to 8

Using process conditions analogous to those described in Example 1 (b) (i) or (iii), the following amines were prepared:

2-methylamino-4-methyloxazole, m.p. 61–3° C.
2-butylamino-4-hydroxymethyloxazole, m.p. 57–9° C.
2-(p-chlorobenzylamino)-4-methyloxazole, m.p. 110–1° C.
5-hydroxymethyl-2-butylamino oxazole, m.p. 87–8° C.
2-benzylamino-4-methyloxazole, m.p. 112° C.
2-hexylamino-4-methyloxazole, b.p. 86–8° C./0.03 mm.
2-pentylamino-4-methyloxazole, b.p. 87° C./1.0 mm.

EXAMPLE 9

2-(N-Butylisobutyramido)-4-methyloxazole

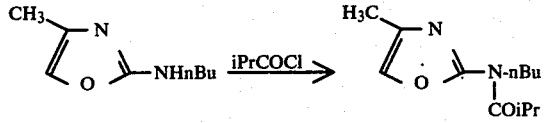

2-(N-butylamino)-4-methyloxazole (106.7 g., 0.69 m.) and triethylamine (110 g., 0.77 m.) was stirred together in dry benzene (1500 c.c.) during the addition of isobutyrylchloride (81.0 g., 0.76 m.). The mixture was stirred at room temperature for 15 hours and then water (1 litre) was added. After stirring for a further hour the organic phase was separated, and the aqueous phase extracted twice in ether. The combined extract was washed successively with 2N hydrochloric acid (2 × 500 c.c.), 10% sodium carbonate solution (2 × 500 c.c.), and saturated brine (2 × 500 c.c.). Evaporation of the dried organic phase gave an oil, which was distilled to give 2-(N-butylisobutyramido)-4-methyloxazole, (118 g., 80%), b.p. 75–76° C./0.15 mm., which existed as an oil at room temperature but crystallised on cooling to 0° C.

Found: C, 64.43; H, 9.06; N, 12.21; O, 14.02%
Calculated for $C_{12}H_{20}N_2O_2$ : C, 64.26; H, 8.98; N, 12.49; O, 14.26%

EXAMPLE 10

2-(N-Butyl-pivalamido)-4-methyloxazole b.p. 89–91° C./0.35 mm., was prepared in a similar manner to that of Example 2, heating the reaction under reflux for 9 hours.

Found: C 65.25; H 9.09; N 11.51%
Calculated for $C_{13}H_{22}N_2O_2$: C 65.51; H 9.31; N 11.76%

EXAMPLE 11

2-(N-Butylcyclobutanecarboxamido)-4-methyloxazole b.p. 107–8° C./0.2 mm. was prepared in a manner similar to Example 9 heating the reaction mixture under reflux for 1 hour.

Found: C 66.22; H 8.30; N 11.63%
Calculated for $C_{13}H_{20}N_2O_2$: C 66.07; H 8.53; N 11.86

EXAMPLE 12

2-(N-Butyl-cyclopentanecarboxamido)-4-methyloxazole b.p. 109–110° C./0.15 mm. was prepared in a manner similar to Example 9, heating the reaction mixture under reflux for 2 hours.

Found: C 66.97; H 8.65; N 11.44%
Calculated for $C_{14}H_{22}N_2O_2$: C 67.17: H 8.86: N 11.19%

EXAMPLE 13

2(N-Butyl-butyramido)-4-methyloxazole, b.p. 96–98° C./1 mm., was prepared in a manner similar to Example 9.

Found: C 63.98; H 8.88; N 12.76%
Calculated for $C_{12}H_{20} N_2O_2$: C 64.26; H 8.98; N 12.49%

EXAMPLE 14

2-(N-Butyl-isobutyramido)-4,5-dimethyloxazole

2-Butylamino-4,5-dimethyloxazole, b.p. 79–81° C./0.1 mm. was prepared in a manner similar to that described in Example 1 using acetoin, and was acylated as described in Example 9 to give the product, b.p. 78–79° C./0.06 mm.

Found: C 65.33; H 9.45; N 11.56%
Calculated for $C_{13}H_{22}N_2O_2$: C65.51; H 9.31; N 11.76%

EXAMPLE 15

2-(N-Butyl-benzamido)-4-methyloxazole, b.p. 118–120° C./0.1 mm. was similarly prepared as in Example 9, heating the reaction mixture under reflux for 1½ hours.

Found: C 69.55; H 6.81; N 11.05%
Calculated for $C_{15}H_{18}N_2O_2$: C 69.74; H 7.02; N 10.85%

EXAMPLE 16

2-(N-Butyl-4-chlorobenzamido)-4-methyloxazole, b.p 136–138° C./0.15 mm. was similarly prepared as in Example 9 stirring the reaction mixture for 24 hours at room temperature.

Found: C 61.67; H 5.61; N 9.34; Cl 12.30%
Calculated for $C_{15}H_{17}ClN_2O_2$: C 61.54; H 5.85; N 9.57; Cl 12.11%

EXAMPLE 17

2-(N-Butyl-isobutyramido)-4-methyloxazole

2-N-butylamino-4-methyloxazole (15.0 gm., 0.0974 mole) and isobutyric anhydride (22 c.c.) were heated at 90° C. for fifteen minutes. The mixture was then allowed to cool and stirred for 1 hour. Excess reagent was removed by evaporation and distillation of the resultant red oil yielded the desired compound, b.p. 75–6° C./0.15 mm. wt=16.1 g. Yield=74%.

EXAMPLE 18

2-(N-Butyl-propionamido)-4-methyloxazole

The procedure of Example 17 was followed using 15.0 g (0.0974 m.) of 2-N-butylamino-4-methyloxazole and 25 c.c. of propionic anhydride.

B.p.=73–75° C./0.15 mm. Wt=12.9 g. Yield=63%

EXAMPLE 19

2-Amino-4-methyloxazole

5N Sodium hydroxide solution (125 ml.) was added dropwise to a stirred solution of hydroxyacetone (74 g., 1mol) and cyanamide (42 g., 1 mol) in water (110 ml.). The mixture rapidly became hot and was cooled to 20° C. and stirred at this temperature for 1 hour and then extracted with ether (3 × 250 ml.). The ether extract was washed with sodium chloride solution, dried over sodium sulphate and then evaporated under vacuum. The residue was distilled under vacuum to give the product 76.8 g. (78%) b.p. 66–67° C./0.5 mm. $n_d^{23}$ 1.495.

EXAMPLE 20

2-(2-Ethylbutryamido)-4-methyloxazole
-Ethylbutyramido)-

A stirred solution of 2-amino-4-methyloxazole prepared as described in Example 19 (8.8 g., 0.089 mol) and 2-ethylbutyric anhydride (19.0 g., 0.089 mol) in toluene (50 ml) was heated under reflux for 2 hours. The cooled solution was washed with sodium carbonate solution, then with sodium chloride solution, dried over sodium sulphate and evaporated. The solid residue was recrystallised from ethyl acetate-petroleum spirit giving white crystals. 10.1 g. (58%) m.p. 106° C.

EXAMPLES 21 - 34

By appropriate modification of the starting materials and reaction conditions described in Example 20, the following amides were prepared:

2-isobutyramido-4-methyloxazole, m.p. 10°–111° C.
2-trifluoroacetamido-4-methyloxazole, m.p. 173°–5° C.
2-butyramido-4-methyloxazole, m.p. 99° C.
2-butyramido-4-ethyloxazole, m.p. 85° C.
2-isobutyramido-5-ethyloxazole, m.p. 118° C.
2-acetamido-4-ethyloxazole, m.p. 96°–8° C.
2-trifluoroacetamido-4-ethyloxazole, m.p. 143° C.
2-isobutyramido-5-methyloxazole, m.p. 109° C.
2-hexanamido-4-methyloxazole, m.p. 66° C.
2-valeramido-4-methyloxazole, m.p. 84°–5° C.
2-butyramido-4,5-dimethyloxazole, m.p. 82°–3° C.
2-propionamido-4,5-dimethyloxazole, m.p. 119°–120° C.
2-propionamido-4-methyloxazole, m.p. 113°–4° C.

EXAMPLE 35

2-(N-Ethyl-2-ethylbutyramido)-4-methyloxazole

Sodium hydride (2.8 g. of a 50% dispersion in oil, 0.058 mol) was added in small portions to a stirred solution of 2-(2-ethylbutyramido)-4-methyloxazole (8.0 g., 0.041 mol) in dimethylformamide (100 ml.) at −5° to 0° C. The mixture was stirred for 2 hours at room temperature and then ethyl iodide (4.7 ml. 0.058 mol) was added. The mixture was stirred for a further 2 hours at room temperature and then poured onto ice-water (250 ml.) and extracted with ether (3 × 100 ml.). The extract was washed with dilute hydrochloric acid, then with sodium chloride solution, dried over sodium sulphate and evaporated. The residue was distilled under vacuum to give the product 4.7 g. (51%) b.p. 71–72° C/0.3 mm.

Found: C 64.10; H 8.69; N 12.35%
Expect for $C_{12}H_{20}N_2O_2$: C 64.26; H 8.98; N 12.49%

EXAMPLE 36

2-(4-Chlorobutyramido)-4-methyloxazole

2-Amino-4-methyloxazole (5.0 g., 0.0509 mol) was dissolved in dry benzene (100 mls.) and triethylamine (5.70 g., 0.0563 mol) was added. The mixture was stirred vigorously at room temperature and 4-chlorobutyrylchloride (7.88 g., 0.0558 mol) in dry benzene (50 mls.) was added rapidly. After the addition the mixture was heated under reflux for 2 hours. The mixture was then cooled and filtered. The filtrate was placed in a separating funnel and washed successively with water (1 × 100 mls.), 10% $Na_2CO_3$ (2 × 100 mls.) and water (3 × 100 mls.). The organic layer was dried over magnesium sulphate and evaporated under vacuum. The product was recrystallised from ethyl acetate/hexane. Wt. = 2.47 g.m.p. 98° C. (Yield = 23.92%).

EXAMPLE 37

1-(4-methyloxazol-2-yl)-2-pyrrolidone

2(4-Chlorobutyramido)-4-methyloxazole (2.20 g., 0.018 mol) prepared as described in Example 36 was dissolved with stirring under nitrogen in dry benzene (350 mls.) and 1:5-diazobicyclo[4,3,0]non-5-ene (1.47 g., 0.0118 mol) in dry benzene (50 mls.) was added with stirring over 10 minutes. The mixture was stirred at room temperature, wrapped in foil overnight. The organic layer was washed with water (3 × 100 mls.) dried over magnesium sulphate and evaporated under vacuum. The product was recrystallised from ethyl acetate/hexane. WT.=0.75 g. m.p. 116° C. (Yield =41.57%).

EXAMPLE 38

2-(N-Butylamino)-4-phenyloxazole

The procedure as described in Example 1 was followed using phenacyl alcohol and butylcyanamide. A colourless oil was obtained after distillation of the product.

Wt. Wt.=5.0 g., 47% Yield. b.p. 134° C/0.1 mm., which crystallised on standing. The analytical sample which separated as needles from petrol (40–60° C.) had m.p. 52–53° C.
Found: C 71.9; H 7.2; N 13.2%
$C_{13}H_{16}N_2O$ requires: C 72.2; H 7.45; N 12.95%

EXAMPLE 39

2-(N-Butyl-isobutyramido)-4-phenyloxazole 2-(N-butylamino)-4-phenyloxazole was acylated with isobutyryl chloride as described in Example 9. An almost colourless oil was obtained on distillation. WT.=4.9 g., b.p. 140° C. (air-bath temperature)/1 mm., 80%.
$C_{17}H_{22}N_2O_2$ requires: C 71.3; H 7.7; N 9.8%
Found: C 71.4; H 7.5; N 9.6%

EXAMPLE 40

2-(N-Butylamino)-4-isopropyloxazole

The procedure of Example 1 was followed using the keto acetate, $(CH_3)_2$

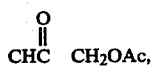

and butylcyanamide.

Distillation gave a colourless product (3.5 g., 68%) b.p. 130° C.(airbath temperature)/0.3 mm.
$C_{10}H_{18}N_2O$ requires: C 66.0; H 10.0; N 15.4%
Found: C 65.8%; H 10.2; N 15.1%

EXAMPLE 41

2-(N-Butyl-isobutyramido)-4-isopropyloxazole 2-(N-Butylamino)-4-ispropyloxazole was acylated with isobutyryl chloride as described in Example 9.
Distillation gave a colorless oil (4.5 g., 68%), b.p. (air-bath) 145° C./0.7 mm.
$C_{14}H_{24}N_2O_2$ requires: C 66.7; H 9.6; N 11.1%
Found: C 66.7; H 10.0; N 10.9%

EXAMPLE 42

2-(N-Butylacetamido)-4-methyloxazole

The procedure of Example 17 was followed using 15.0g. (0.0974 m) of 2-butylamido-4-methyl oxazole and 25 c.c. of acetic anhydride.
B.p.=58–60° C./0.1 mm. wt.=14.4 g. yield=75.4%.

EXAMPLE 43

2-(N-Benzylisobutyramido)-4-methyloxazole, was suitably prepared as in Example 9.
B.p.=124° C./0.6 mm wt.=7.2. g.

EXAMPLE 44

2-(N-[3-chlorobenzyl]isobutyramido)-4-methyloxazole 2-iso Butyramido-4-methyloxazole (11.1 g., 0.066 mol) prepared in a manner similar to that described in Example 20, was dissolved in dry dimethylformamide. Solid potassium carbonate (10.47 g., 0.076 mol) and 3-chlorobenzyl bromide (15.6 g., 0.076 mol) were added and the stirred mixture was heated at 70° C. for 2 hours, cooled and poured into cold water. The solution was extracted with ether and the extract was dried over magnesium sulphate and evaporated. The residue was distilled to give the product, 12.3 g., b.p. 115–120° C./0.08 mm.

EXAMPLES 45 – 171

Using analogous procedures to those utilised in Examples 1 to 44, the following compounds were prepared:

2-(N-butylpentanimido)-4-methyloxazole, b.p. 88–91° C./0.2 mm.

2-(N-butylhexanamido)-4-methyloxazole, b.p. 102° C./0.3 mm.

2-(N-butyl-2-ethylbutyramido)-4-methyloxazole, b.p. 127° C./2.5 mm.

2-(N-butylcyclopropanecarboxamido)-4-methyloxazole, b.p. 97–100° C./0.5 mm.

2-(N-butylcyclohexanecarboxamido)-4-methyloxazole, m.p. 46.5–48.5° C.

2-(N-butylcycloheptanecarboxamido)-4-methyloxazole, b.p. 138–141° C./1 mm.

2(N-butylphenylacetamido)-4-methyloxazole, b.p. 126–130° C./0.2 mm.

2-(N-butyl-3-phenylpropionamido)-4-methyloxazole, b.p. 137–138° C./0.2 mm.

2-(N-butyl-2-chlorobenzamido)-4-methyloxazole, b.p. 130–131° C./0.2 mm.

2-(N-butyl-3-chlorobenzamido)-4-methyloxazole, b.p. 145–147° C./0.4 mm.

2-(N-butyl-2-methoxybenzamido)-4-methyloxazole, b.p. 158–160° C./0.8 mm.

2-(N-butyl-4-methoxybenazmido)-4-methyloxazole, b.p. 162–163° C./1.0 mm.

2-(N-butyl-4-toluamido)-4-methyloxazole, b.p. 139–140° C./0.7 mm.

2-(N-butyl-3-trifluoromethylbenzamido)-4-methyloxazole, b.p. 114–115° C./0.3 mm.

2-(N-butyl-4-nitrobenzamido)-4-methyloxazole, b.p. 178–180° C./1.0 mm.

2-(N-methylacetamido)-4-methyloxazole, m.p. 27–29° C.

2-(N-methylisobutyramido)-4-methyloxazole, b.p. 49–50° C./0.35 mm.

2-(N-ethylacetamido)-4-methyloxazole, b.p. 50–51° C./0.05 mm.

2-(N-ethylbutyramido)-4-methyloxazole, b.p. 63–64° C./0.1 mm.

2-(N-isopropylacetamido)-4-methyloxazole, b.p. 75° C./3.0 mm.

2-(N-isopropylpropionamido)-4-methyloxazole, b.p. 65° C./0.5 mm.

2-(N-isopropylbutyramido)-4-methyloxazole, b.p. 69° C./0.35 mm.

2-(N-isopropylisobutyramido)-4-methyloxazole, b.p. 60–62° C./0.4 mm.

2-(N-s-butylacetamido)-4-methyloxazole, b.p. 64° C./0.6 mm. 2-(N-s-butylpropionamido)-4-methyloxazole, b.p. 76° C./0.4 mm.

2-(N-s-butylbutyramido)-4-methyloxazole, b.p. 75–76° C./0.5 mm.

2-(N-s-butylisobutyramido)- 4-methyloxazole, b.p. 82° C./0.8 mm.

2(N-hexylacetamido)-4-methyloxazole, b.p. 96–92° C./0.08 mm.

2-(N-hexyisobutyramido)-4-methyloxazole, b.p. 106–109° C./1.0 mm.

2-(N-benzylacetamido)-4-methyloxazole, b.p. 119–120° C./0.3 mm.

2-(N-benzylpropionamido)-4-methyloxazole, b.p. 132–133° C./0.3 mm.

2-(N-benzylbutyramido)-4-methyloxazole, b.p. 128° C./0.15 mm.

2-(N-propylpentanamido)-4-methyloxazole, b.p. 83–84° C./0.2 mm.

2-(N-[2-methoxyethyl]acetamido)-4-methyloxazole, b.p. 84° C./0.6 mm.

2-(N-[2-methoxyethyl]propionamido)-4-methyloxazole, b.p. 88° C./0.4 mm.

2(N-2-methoxyethyl]butyramido)-4-methyloxazole, b.p. 96° C./0.4 mm.

2-(N-[2-methoxyethyl]-2-ethylbutyramido)-4-methyloxazole, b.p. 98° C./C./0.4 mm.

2-(N-[2-methoxyethyl]isobutyramido)-4-methyloxazole, b.p. 84–85° C./0.05 mm.

2-(N-[2-methoxyethyl]isobutyramido)-4-methyloxazole, b.p. 84–85° C./0.05 mm.

2-(N-allylacetamido)-4-methyloxazole, b.p. 67° C./0.8 mm.

2-(N-allylpropionamido)-4-methyloxazole, b.p. 75° C./0.8 mm.

2-(N-allylbenzamido)-4-methyloxazole, b.p. 119° C./0.7 mm.

2-(N-allylbutyramido)-4-methyloxazole, b.p. 76° C./0.6 mm.

2-N-allyl-2-ethylbutyramido)-4-methyloxazole, b.p. 83° C./0.65 mm.

2-(N-ethylacetamido)-4,5-dimethyloxazole, b.p. 61–62° C./0.3 mm.

2-(N-ethylpropionamido)-4,5-dimethyloxazole, b.p. 68–69° C./0.3 mm.

2-(N-ethylpropinamido)-4,5-dimethyloxazole, b.p. 68–69° C./0.3 mm.

2-(N-ethylbutyramido)-4,5-dimethyloxazole, b.p. 68–70° C./0.25 mm.

2-(N-ethylisobutyramido)-4,5-dimethyloxazole, b.p. 63–65° C./0.25 mm.

2-(N-butylacetamido)-4,5-dimethyloxazole, b.p. 89–91° C./1.0 mm.

2-(N-butylpropinoamido)-4,5-dimethyloxazole, b.p. 86–88° C./0.4 mm.

2-(N-butylisobutyramido)oxazole, b.p. 120° C./0.5 mm.*

2-(N-butylisobutyrmido)-4-cyclohexyloxazole, b.p. 165° C./0.4 mm.*

2-(N-butylisobutyramido)-4-butyloxazole, b.p. 140° C./0.05 mm.*

2-(N-butylacetamido)-5-acetoxymethyloxazole, b.p. 170° C./0.5 mm.*

5-isobutyroxymethyl-2-(N-butylisobutyramido)oxazole, b.p. 180° C./0.5 mm.*

5-cyclohexyl-2(N-butylisobutyramido)-oxazole, b.p. 170° C./0.5 mm.

2-(N-cyclopentylvaleramido)-4-methyloxazole, b.p. 102°–104° C./0.2 mm.

2-(N-2'-methoxyethylcyclopentanecarboxamido)-4-methyloxazole, b.p. 117° C./1.0 mm.

2-(N-2'-phenethylpropionamido)-4-methyloxazole, b.p. 126° C./0.6 mm.

2-(N-2'-phenethylacetamido)-4-methyloxazole, b.p. 122° C./0.5 mm.

2-(N-allylisobutyramido)-4-methyloxazole, b.p. 68° C./0.5 mm.

2-(N-β-phenethylbutyramido)-4-methyloxazole, b.p. 133° C./0.7 mm.

2-(N-β-phenethylisobutyramido)-4-metnyloxazole, b.p. 128° C./0.65 mm.

4-isobutyroxymethyl-2-(N-butylisobutyramido)oxazole, b.p. 180° C./0.5 mm.*

2-(N-butylbenzamido)-4,5-dimethyloxazole, b.p. 125°–128° C./0.5 mm.

2-(N-butylvaleramido)-4,5-dimethyloxazole, b.p. 102°–105° C./0.5 mm.

2-(N-butylcyclobutanecarboxamido)-4,5-dimethyloxazole, b.p. 105°–107° C./0.5 mm.

2-(N-butylbutyramido)-4,5-dimethyloxazole, b.p. 95–98° C./0.5 mm.

2-(N-butyl-3-nitrobenzamido)-4-methyloxazole, b.p. 152°–155° C./0.2 mm.

2-(N-[2-methylbutyl]-butyramido)-4-methyloxazole, b.p. 87° C./0.5 mm.

2-(N-[2-methylbutyl]-propionamido)-4-methyloxazole, b.p. 82°–83° C./0.5 mm.

2-(N-(2-methylbutyl]-isobutyramido)-4-methyloxazole, b.p. 83° C./0.5 mm.

2-(N-pentylbenzamido)-4-methyloxazole, b.p. 130° C./0.7 mm.

2-(N-cyclohexylpropionamido)-4-methyloxazole, b.p. 101° C./0.5 mm.

2-(N-ethylhexanamido)-4-methyloxazole, b.p. 94°–96° C./0.7 mm.

2-(N-butylcyclohexanecarboxamido)-4,5-dimethyloxazole, b.p. 122°–126° C./0.5 mm.

2-(N-butylcyclopentanecarboxamido)-4,5-dimethyloxazole, b.p. 112°–116° C./0.5 mm.

2-(N-cyclohexylbutyramido)-4-methyloxazole, b.p. 118° C./0.7 mm.

2-(N-butyl-3,4-dichlorobenzamido)-4-methyloxazole, b.p. 162°–165° C./1.0 mm.

2-(N-pentylbutyramido)-4-methyloxazole, b.p. 98° C./0.8 mm.

2-(N-benzylbenzamido)-4-methyloxazole, m.p. 62° C.

2-(N-benzylvaleramido)-4-methyloxazole, b.p. 134° C./0.7 mm.

4,5-dimethyl-2-(N-methylacetamido)oxazole, m.p. 40°–42° C.

2-(N-butyl-1-adamantanecarboxamido)-4-methyloxazole, b.p. 160° C./0.3 mm.

2-(N-ethyl-2-ethylbutyramido)-4-methyloxazole, b.p. 71°–2° C./0.3 mm.

2-(N-butyl-4-fluorobenzamido)-4-methyloxazole, b.p. 120°–2° C./0.3 mm.

4-methyl-2-(N-propyl hexanamido)oxazole, b.p. 96°–8° C./0.4 mm.

4-methyl-2-[N-(1-ethylpropyl)-butanamido]oxazole, b.p. 58°–60° C./0.5 mm.

4-methyl-2-[N-(1-ethylpropyl)-pentamido]oxazole, b.p. 91° C./0.5 mm.

2-(N-pentyl propanamido)-4-methyloxazole, b.p. 68° C./0.05 mm.

2-(N-pentyl isobutyramido)-4-methyloxazole, b.p. 86°–7° C./0.4 mm.

2-(N-butyl isobutyramido)-4-ethyloxazole, b.p. 140° C./0.5 mm.*

2-(N-isopropyl pentanamido)-4-methyloxazole, b.p. 77° C./0.3 mm.

2-(N-butyl dichloroacetamido)-4-methyloxazole, b.p. 112°–4° C./0.8 mm.

2-(N-p-chlorobenzyl isobutyramido)-4-methyloxazole, b.p. 136° C./0.7 mm.

2-(N-hexyl propanamido)-4-methyloxazole, b.p. 106°–8° C./1.0 mm.

2-(N-butyl chloroacetamido)-4-methyloxazole, b.p. 96°–8° C./1.0 mm.

2-(N-butyl isobutyramido)-4-methyl-5-hydroxyoxazole (−) 2-(N-but-2-yl butanamido)-4-methyloxazole, b.p. 86°-9° C./1.2 mm.
(+) 2-(N-but-2-yl butanamido)-4-methyloxazole, b.p. 85°-8° C./1.5 mm.
2-(N-butyl-N-isobutyramido)-4-hydroxymethyloxazole, b.p. 185° C./0.3 mm.*
2-(N-benzyl hexanamido)-4-methyloxazole, b.p. 144° C./0.6 mm.
2-(N-butyl-4-chlorobutanamido)-4-methyloxazole, b.p. 124°-8° C./1.2 mm.
2-(N-prop-1-yn-3-yl-isobutyramido)-4-methyloxazole, b.p. 87° C./0.5 mm.
2-(N-butyl isobutyramido)-4-p-chlorophenyloxazole, b.p. 200° C./0.5 mm.*
2-(N-butyl-isobutyramido)-5-methyloxazole, b.p. 100° C./0.1 mm.*
1-(4-methyl oxazol-2-yl)-2-oxo-hexahydro-1H-azepine, b.p. 130° C./0.1 mm.*
2-(N-cyclopentyl isobutyramido)-4-methyloxazole, m.p. 73° C.
D(−) 2-(N-butyl-2-methylbutanamido)-4-methyloxazole, b.p. 88°-92° C./0.6 mm.
L(+) 2-(N-butyl-2-methylbutanamido)-4-methyloxazole, b.p. 88°-91° C./0.6 mm.
2-(N-butyl-2-methylbutanamido)-4-methyloxazole, b.p. 82°-5° C./0.2 mm.
2(N-butyl acetamido)-4-carbethoxyoxazole, b.p. 170° C./0.1 mm.*
2-N-(butylisobutyramido)-5-phenyloxazole, b.p. 190° C./0.2 mm.*
2-[N-(3-carbethoxypropyl)isobutyramido]-4-methyloxazole, b.p. 122°-5° C./0.4 mm.
2-(N-cinnamyl isobutyramido)-4-methyloxazole, b.p. 152°-156° C./1.0 mm.
2-[N-(4-methylbenzyl)isobutyramido]-4-methyloxazole, b.p. 120°-4° C./0.3 mm.
2-[N-(3-methylbenzyl)isobutyramido]-4-methyloxazole, b.p. 118°-122° C./0.3 mm.
2-(N-butyl-heptanamido)-4-methyloxazole, b.p. 106°-8° C./0.05 mm.
2-(N-butyl cyclopentylacetamido)-4-methyloxazole, b.p. 124°-6° C./0.8 mm.
2-(N-cyclohexylmethyl isobutanamido)-4-methyloxazole, b.p. 122°-4° C./0.8 mm.
2-[N-(4-methoxybenzyl)isobutyramido]-4-methyloxazole, b.p. 145°-8° C./0.4 mm.
2-(N-butylcinnamamido)-4-methyloxazole, b.p. 200° C./0.2 mm.
2-[N-(3-carboxypropyl)octanamido]-4-methyloxazole, b.p. 200° C./0.2 mm.
2-[N-(3-carbethoxypropylpentanamido]-4-methyloxazole, b.p. 142°-5° C./0.6 mm.
2-[N-(3-chloropropyl)pentanamido]-4-methyloxazole, b.p. 118°-122° C./0.7 mm.
2-[N-(3-chloropropyl)isobutyramido]-4-methyloxazole, b.p. 99°-102° C./0.5 mm.
2-(N-butylbut-2-enamido)-4-methyloxazole, b.p. 150° C./0.02 mm.
2-(N-butylisobutyramido)-5-ethyloxazole, b.p. 70°-72° C./0.2 mm.
2-(N-butyltrifluoroacetamido)-4-methyloxazole, b.p. 67°-69° C./0.8 mm.

*Temperature recorded in an air-bath.
Boiling point not taken but mass-spectral data in accord with structure.

Microanalysis (C,H,N) for each of the compounds listed in Examples 45 - 171 was (within the limits of experimental error) equal to the expected theoretical result. In addition, infra-red, ultra-violet and proton magnetic resonance spectra were consistent with the assigned structures.

EXAMPLE 172

5-Hydroxy-2(N-butylisobutyramido)-4-methyloxazole 4-methyl-2(N-butylisobutyramido)oxazole (15 g., 0.067 m.) in dry methylene chloride (100 c.c.) was cooled to 0° C. during the addition of m-chloroperbenzoic acid (16 g., 0.023 m.) over 1 hour. The mixture was then stirred at room temperature for 40 hours. The precipitated m-chlorobenzoic acid was then filtered off and the filtrate evaporated to dryness. The residue was taken in ether (100 c.c.) and stirred with 5% aqueous sodium sulphite solution for 1 hour. The organic phase was then separated and washed successively with aqueous sodium carbonate ($\times 2$) and water, and then dried and evaporated to give a brown oil, 13.9 g.

A portion of the above product (10 g.) was dissolved in ether and washed with 1N NaOH (2 $\times$ 25 c.c.). The cooled aqueous phase was acidified with 2N hydrochloric acid and extracted into ether. The washed (aqueous $Na_2CO_3$ and water) organic phase was dried and evaporated to give a yellow oil (4.05 g.). The product was then chromatographed on a column of alumina (Brockman grade II, 200 g.). Elution with ethyl acetate removed less polar impurities, whilst the product (2.5g.) was eluted with 5% MeOH/ethylacetate.

$C_{12}H_{20}N_2O_3$ requires: C 60.1; H 8.4; N 11.7% Found: C 59.8; H 8.4; N 11.7%

The product was further characterised by conversion into its methyl ether with silver oxide and methyl iodide in DMF.

$C_{13}H_{22}N_2O_3$ requires: C 61.5; H 8.7; N 11.0% Found: C 61.6%; H 8.8; N 11.3%

EXAMPLE 173

(a) 2-isobutyramido-5-methyloxazole

2-Amino-5-methyloxazole (3.30 g., 0.0336 mol) prepared by the method of Berichte 95 2419 (1962) was added to dry benzene (40 ml.) and isobutyric anhydride (5.90 g., 0.0372 mol) was added. The mixture was heated under reflux for 3 hours. Methanol (5 ml.) and triethylamine (5 drops) were then added cautiously and the mixture was heated for a further 30 minutes. The mixture was then cooled and washed with water (2 $\times$ 20 mls.), 10% aqueous sodium carbonate (3 $\times$ 25 mls.) and water (3 $\times$ 20 mls.). The organic phase was then dried over magnesium sulphate and evaporated under reduced pressure. The solid was then recrystallised from hexane Yield = 1.44 g. (25.5%) m.p. 109°-109.5° C.

Analysis Th. for $C_8H_{12}N_2O_2$
Th. C 57.13% H 7.19% N 16.66% O 19.02% Fd. C 57.40% H 7.20% N 16.52% O 19.07%

(b) 2-(N-butyl-isobutyramido)-5-methyloxazole

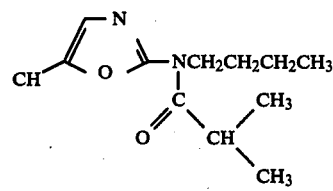

2-isobutyramido-5-methyloxazole (2.10 g., 0.0124 mol), prepared as above, was dissolved in dry dimethylformamide (10 mls.) and cooled to below 5° C. To this was added sodium hydride (0.70 g., 0.0145 mol.) portionwise, keeping the temperature below 5° C. After the addition, the mixture was stirred for a further 30 minutes at 5° C. and then allowed to warm to room temperature. The iodobutane (5.0 g., 0.0271 mol.) was added. The mixture was stirred overnight, the solvent was evaporated under reduced pressure and the residue was partitioned between water (50 mls.) and ether (50 mls.). The organic phase was then washed with 2N HCl (2×25 mls.), water (1×25 mls.), 10% aqueous sodium carbonate (3×25 mls.) and water (3×25 mls.). The organic phase was then dried over magnesium sulphate and evaporated under reduced pressure. The residue was distilled from a Kugelrohr, air bath temperature 100° C./0.1 mm. Yield=1.74 g. (62%).

Analysis for $C_{12}H_{20}N_2O_2$
Th. C 64.26% H 8.98% N 12.49% Fd. C 64.08% H 8.73% N 12.21%

EXAMPLE 174

4-Formyl-2-(N-Butylisobutyramido)-oxazole

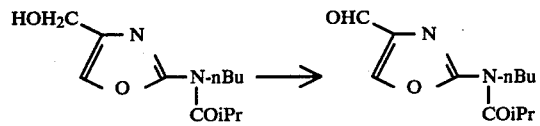

The alcohol (5 g., 0.0206 m.) was added to a stirred solution of chromium trioxide (14.8 g.) and pyridine (23.6 g.) in methylene chloride (600 c.c.). The mixture was stirred at room temperature for 15 minutes, and then filtered and evaporated. Ether was added to the residue and the mixture was again filtered and evaporated. The resulting pale brown oil was distilled at 150° C. (air-bath)/0.2 mm., as a colourless oil 3.1 g., 63%.

$C_{12}H_{18}N_2O_3$ requires: C 60.6; H 7.6; N 11.8% Found: C 60.4; H 7.9; N 11.55%

EXAMPLE 175

4-Carboxy-2-(N-butylisobutyramido)-oxazole

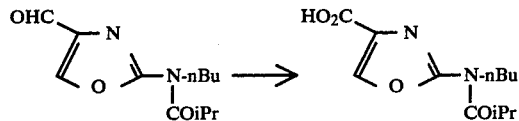

The aldehyde (3 g., 0.0126 m.) was stirred in THF/water (9:1) (80 c.c.) with Ag (II)O (15 g.) for 15 hours. The solution was then filtered and the residue washed in methanol.

THF and methanol were then removed in vacuo, and the residue was dissolved in ether, and stirred for 1 hour with 2N HCl.

Separation of the ether layer, drying and evaporation gave the crude acid (1.5 g.), which was distilled at 180° C. (air-bath)/0.25 mm. to give a crystalline solid, 1.1 g., 34%. The acid was recrystallised from hexane as fine white needles m.p. 70°-72° C.

$C_{12}H_{18}N_2O_4$ requires C 56.75; H 7.1; N 11.0% Found: C 56.8; H 7.2; N 10.8%

EXAMPLE 176

5-(N-butyl-trifluoroacetamido)-2-methyloxazole

2-Acetamido-N-butylacetamide (18.70 g, 0.1085 mol) made by the method in J. A. C. S. 71 2899(1949), was dissolved in dry chloroform (200 ml.) and trifluoroacetic anhydride (45.06 g., 0.2170 mol) was added dropwise with stirring under nitrogen. Heat was evolved. The mixture was stirred for 4 hours under nitrogen and then solid anhydrous sodium carbonate (50.0 g., 0.4717 mole) was added portionwise with stirring. After 30 minutes, solid was filtered off and was washed with dry chloroform (2×25 ml.). The combined filtrates were evaporated under reduced pressure. The oil was then distilled under vacuum to give the desired product 11.37 g. (42%) b.p. 51°-2° C./0.1 mm.

The product was a colourless oil.

Required for $C_{10}H_{13}N_2O_2F_3$ C 48.00% H 5.2% N 11.20% F 22.78% Found C 47.72% H 5.08% N 10.93% F 22.62%

EXAMPLE 177

(a) 2-Benzamido-N-benzyl-N-methylpropanamide

N-Benzoylalanine cyanomethyl ester (29.80 g., 0.1283 mol), prepared by the method described in Bull. Soc. Chem. Fr. 3127 (1973), was dissolved in ethyl acetate (300 mls.) and benzylmethylamine (31.10 g., 0.2566 mol) was added. The reaction mixture was stirred at room temperature for 7 days and then the mixture was washed with 2N HCl (6×50 mls.) water (1×50 mls.), 10% aqueous sodium carbonate (2×50 mls.), and finally water (3×50 mls.). The organic phase was dried over magnesium sulphate and evaporated under reduced pressure to give a dark oil. This was chromatographed on silica using chloroform to give a partially purified material. This was then distilled from a Kugelrohr airbath apparatus at 230° C., pressure 0.01 mm. to give a pale yellow oil.

(b) 5-(N-benzylmethylamino)-4-methyl-2-phenyloxazole

2-Benzamido-N-benzyl-N-methylpropanamide (8.0 g., 0.0269 mol.), was dissolved in dry chloroform (40 ml.) and trifluoroacetic anhydride (17.0 g., 0.0809 mol.) was added dropwise with stirring under nitrogen. The mixture was stirred for 4 hours, then sufficient anhydrous sodium carbonate was added portionwise to neutralise the acid formed. The solid was filtered off and washed with dry chloroform (2×10 ml.). The combined filtrates were evaporated under reduced pressure to give a brown oil, which was extracted with warm pentane. The pentane solution was evaporated to give a yellow oil 6.20 g. (82.5% IR and NMR confirm the structure.

(c) 5-(N-methyl acetamido)-4-methyl-2-phenylaoxazole

10% Palladium/charcoal catalyst (0.30 g.) was weighed out and acetic anhydride (30 mls.) was cautiously added under nitrogen.

5-(N-Benzylmethylamino)-4-methyl-2-phenyloxazole (3.0 g., 0.0167 mole) was added and the mixture was hydrogenated at room temperature and atmospheric pressure for 24 hours. The catalyst was filtered off and the mixture was evaporated under reduced pressure. A sample was purified on preparative thin layer chormatography.

Mass spectra showed the mass ion to be 230 (correct value) and the fragmentation pattern was consistent with the correct product.

EXAMPLE 178

(a) 2-Acetamido-N-benzyl-N-methylacetamide

N-Acetylglycine cyanomethyl ester (96.0 g., 0.6148 mol.), prepared by the method described in Roczniki Chem. 34 1488 (1960), was dissolved in warm ethyl acetate (1 L) and benzylmethylamine (225.0 g. 1.8566 mol.) added with stirring under nitrogen. The mixture was heated under reflux for 2 hours. The solvent was evaporated under reduced pressure. The excess amine was distilled off under vacuum and the residue was then distilled to give a pale yellow viscous oil 90.56 g. (67%) b.p. 160°–165° C./0.05 mm.

(b) 5-(N-benzylmethylamino)-2-methyloxazole

2-Acetamido-N-benzyl-N-methylacetamide (10.0 g., 0.0453 mol.) was stirred under nitrogen at room temperature and phosphoryl chloride (33 mls.) was added rapidly. The mixture was stirred for 4 hours, then the excess reagent was evaporated under reduced pressure. The dark oil was then dissolved in a small amount of chloroform and added slowly to a stirred mixture of sodium carbonate in ice, ensuring that the mixture remained alkaline. The organic phase was then separated and the aqueous phase was extracted with more chloroform. The combined extracts were evaporated to give a dark oil. The dark oil was purified by chromatography on alumina and then distilled. b.p. 130° C./0.1 mm.*

*air-bath temperature.

(c) 5-(N-methyl acetamido)-2-methyloxazole

Using similar reaction conditions to those described in Example 177 (c), the title compound was prepared. Confirmation of its structure was obtained by mass spectra evidence.

EXAMPLE 179

(a) t-Butyl-4-(2-phenyloxazolyl)-carbamate

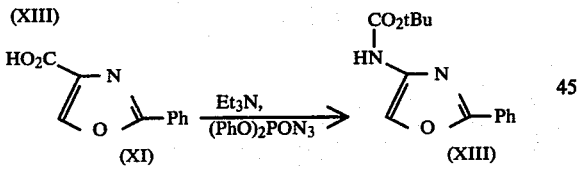

2-Phenyloxazole-4-carboxylic acid (9.45 g., 0.05 m.), prepared by the method of Cornforth and Cookson [J. Chem. Soc. 1086, (1962)], dimethoxyethane (25 c.c), triethylamine (5.05 g., 0.05 m.) and t-butanol (10 c.c), were mixed and cooled at 0° C. in an atmosphere of nitrogen. Diphenylphosphonic azide (10.75 c.c., 0.05 m.) was then added slowly. When the addition was complete, the temperature was raised to 80° C. when evolution of nitrogen was apparent. The temperature was maintained at 80°–90° C. for 2½ hours. The solution was then cooled, diluted with water and extracted in ethyl acetate. The organic extract was washed with aqueous sodium carbonate solution and water, and then dried ($Na_2SO_4$) and evaporated. The resulting brown oil was eluted through a short column of neutral alumina with ether. Evaporation of the eluate gave white crystals, 5.3 g., 44% m.p. 121–125° C.

$C_{14}H_{16}N_2O_3$ requires: C 64.7; H 6.2; N 10.8% Found: C 64.7; H 6.4; N 10.7%

(b) 2-Phenyl-4-isobutyramido-oxazole(XV)

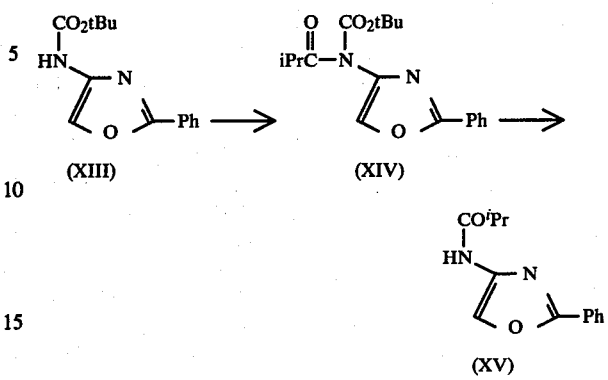

(XIII) (5 g., 0.019 m.) in dry DMF (20 c.c) was cooled at 0° C. under nitrogen. Sodium hydride (1 g., of a 50% suspension) was then added slowly. After a further 30 minutes at 0° C., isobutyryl chloride (2.5 g., 1.8 c.c. 0.0235 m.) was added dropwise. Stirring was continued for 1 hour as the temperature rose to 20° C. Water was then added, and the product isolated in ether. Evaporation of the dried organic extract gave an oil, 5.8 g., which crystallised on standing. A small sample crystallised from petrol (40°–60° C.) as white flakes, m.p. 72°–80° C.

The crude carbamate (XIV) (5.5 g., 0.166 m.) was refluxed in methyl ethyl ketone (25 c.c.) containing anhydrous lithium iodide (2.5 g.) for 15 hours. Solvent was then removed in vacuo, and the residual oil partitioned in ether and water. The aqueous phase was acidified to pH2, and then the ether phase was separated, dried, and evaporated. The resulting brown oil was passed through a silica column with chloroform. Evaporation of the eluate gave a crystalline solid, which separated from ether/petrol (40°–60° C.) as colourless needles, 1.2 g., m.p. 142°–143° C.

$C_{13}H_{14}N_2O_2$ requires: C 67.9; H 6.1; N 12.2% Found: C 67.9; H 6.1; N 12.3%

(c) 2-Phenyl-4(N-butylisobutyramido)oxazole

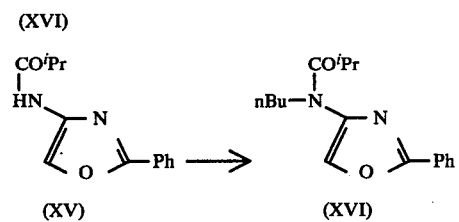

(XV) (1.1 g., 0.0048 m.) was cooled at 0° C. in dry DMF (20 c.c.) and NaH (0.25 g., of 50% dispersion) was added. After 30 minutes at 0° C., butyl iodide (1 g., 0.0052 m.) was added. The temperature rose to 20° C. over a period of 3 hours. Water was then added and the product was isolated in ether. The pale brown extract was passed through a short alumina column with ether, and the colourless eluate was evaporated to dryness. The residue was distilled at 180° C. (air-bath)/0.2 mm. to give XVI as a colourless oil, 1.2 g. 88%.

Examples 180–197

Using process conditions analogous to those described in Example 1 (b) the following amines were prepared:

2-propylamino-4-methyloxazole, b.p. 65°-67° C./0.3 mm,
2-t-butylamino-4-methyloxazole, b.p. 44°-48° C./0.3 mm.
2-cyclopentylamino-4-methyloxazole, m.p. 67° C.
2-s-butylamino-4-methyloxazole, b.p. 68°-70° C./1.0 mm.
(+) 2-s-butylamino-4-methyloxazole b.p. 71°-72° C./1.4 mm.
(−) 2-s-butylamino-4-methyloxazole, b.p. 68°-70° C./1.2 mm.
2(4-methoxybenzylamino)4-methyloxazole, m.p. 94° C.
2-cyclohexylmethylamino-4-methyloxazole, b.p. 110°-113° C./0.8 mm.
2-allylamino-4-methyloxazole, b.p. 62°-64° C./0.4 mm.
2-isopropylamino-4-methyloxazole, b.p. 66° C./0.1 mm.
2(2-methoxyethylamino)4-methyloxazole, b.p. 72°-73° C./0.7 mm.
2(2-phenylethylamino) 4-methyloxazole, b.p. 134° C./0.7 mm.
2(2-methyl-butylamino) 4-methyloxazole, b.p. 101° C./2.5 mm.
2-cyclohexylamino-4-methyloxazole, b.p. 112° C./2.0 mm.
2-pentylamino-4-methyloxazole, b.p. 87° C./1.0 mm.
2-(1-ethylpropylamino)-4-methyloxazole, b.p. 65°-66° C./0.2 mm.
2-ethylamino-4-methyloxazole, b.p. 85°-90° C./8 mm.
2-ethylamino-4,5-dimethyloxazole, b.p. 57°-59° C./0.2 mm.

EXAMPLES 197 to 199

By appropriate modification of the starting materials and reaction conditions described in Example 20, the following amides were prepared:
2-phenylacetamido-4-methyloxazole, m.p. 177° C.
2-octanamido-4-methyloxazole, m.p. 61°-63° C.

EXAMPLE 200

2-[N-(3-Carboxypropyl)-isobutyramido]-4-methyloxazole

A solution of 2[N-(3-carbethoxypropyl)-isobutyramido]-4-methyloxazole (9.9 g., 0.035 mol.) prepared in a manner similar to that described in Example 44 was dissolved in ethanol (100 ml.) and N NaOH solution (35 ml.) and the solution was stirred for 20 hours at ambient temperature. The solution was evaporated and the residue was dissolved in water, washed with ether, acidified and extracted with ether. The extract was dried and evaporated and the residue was recrystallised from benzene—petrol to give the product 5.1 g., m.p. 81°-82° C.

EXAMPLE 201

Similarly prepared was:
2-[N-(3-carboxypropyl)-octanamido]-4-methyloxazole, b.p. 200° C./0.2 mm.

The following Examples 202–210 illustrate pharmaceutical formulations containing the active compound 2-(N-butyl isobutyramido)-4-methyloxazole.

EXAMPLE 202

Soft gelatin capsules were prepared using the following ingredients;

| | Quantity (mg/capsule) |
|---|---|
| Active compound | 25 |
| Butylated hydroxyanisole B.P. | 0.02 |
| Fractionated Coconut Oil B.P.C. | 75 |
| | 100.02 |

The above ingredients were mixed and filled into soft gelatin capsules, the main shell components of which were gelatin and glycerine.

EXAMPLE 203

The procedure of Example 202 was repeated except that an identical quantity of propyl gallate was used in place of the butylated hydroxyanisole as antioxidant.

EXAMPLE 204

Hard gelatin capsules were prepared using the following ingredients

| | Quantity (mg/capsule) |
|---|---|
| Active compound | 25 |
| Silicon dioxide (fumed) | 25 |
| Lactose | 50 |
| Butylated hydroxyanisole B.P. | 0.02 |

The butylated hydroxyanisole was dissolved in the active ingredient and the solution so formed adsorbed onto the silicon dioxide (fumed). The lactose was then added and the whole mixed. Finally, the mixture was filled into hard gelatin capsules.

Alternatively, the solution of butylated hydroxyanisole and active compound can be diluted with an inert solvent, the solution slurried onto the silicon dioxide (fumed) and the inert solvent evaporated off. The lactose is then mixed in and the mixture filled into the hard gelatin capsules.

EXAMPLE 205

An injectible solution was prepared containing the following components:

| | |
|---|---|
| Active ingredient | 25 mg. |
| Cremophor EL | 25 mg. |
| Ethanol | 25 mg. |
| Water | 25 mg. |
| Butylated hydroxyanisole B.P. | 0.02 mg. |

The butylated hydroxyanisole was dissolved in the active ingredient and ethanol, the water and Cremophor EL added and the solution sterilised by filtration through a bacteria proof filter into sterile containers.

EXAMPLE 206

An ointment was made up from the following ingredients

| | |
|---|---|
| Active compound | 1% by weight |
| Butylated hydroxyanisole B.P. | 0.02% by weight |
| White soft paraffin | q.s. 100% |

The hydroxyanisole was dissolved in the melted paraffin and the active compound then added in, and the mixture allowed to cool.

EXAMPLE 207

A topical cream containing 0.5% of the compound is prepared as follows:

|                          | grams      |
|--------------------------|------------|
| Active Compound          | 0.5        |
| Cetomacrogol 1000        | 2.8        |
| Cetostearyl alcohol      | 11.2       |
| Liquid Paraffin          | 8.0        |
| Butylated hydroxyanisole B.P. | 0.02  |
| Distilled water          | to 100.0   |

The compound is mixed with the hydroxyanisole and suspended in the liquid paraffin. The cetostearyl alcohol is added and the mixture heated to 70° C. with stirring. The cetomacrogol 1000 is dissolved in 60 g. of water heated to 70° C. The cetostearyl alcohol and liquid paraffin active compound mixture are then poured into the aqueous cetomacrogol 1000 solution with stirring and the stirring is continued until the cream is cold. The cream is then made up to weight with water and passed through a stainless steel colloid mill set at a gap of 15/1000 inch.

EXAMPLE 208

Suppositories containing 25 and 50 mg. of the compound are prepared as follows:

| Active compound | 2.5 g.  |
|-----------------|---------|
| Henkel base     | 97.5 g. |

The active compound is mixed with the Henkel base which had been previously melted using the minimum amount of heat possible. The mixture is then poured into suppository moulds of a nominal capacity of 1 g. or 2 g. as desired, to produced suppositories each containing 25 mg. or 50 mg. of the active compound.

EXAMPLE 209

An aerosol was prepared containing the following ingredients:

|                                        | Quantity per ml. |
|----------------------------------------|------------------|
| Active compound                        | 10.00 mg.        |
| Propylene glycol                       | 10.00 mg.        |
| Dichlorotetrafluoroethane (Propellant 114) | 562.50 mg.  |
| Dichlorodifluoromethane (Propellant 12) | 829.50 mg.      |

The active compound is mixed with the propylene glycol and the mix added to the propellant 114, the mixture cooled to −15 to −20° C. and transferred to a filling device. At the same time a mixture of propellants 114 and 12, previously cooled to −15° to −20° C. is fed into a second filling device. A metered amount of propellant from the second filling device is introduced into a stainless steel container, followed by the required amount of material from the first filling device. The valve units are then fitted and sealed to the container. These valve units may be equipped with metering device so that approximately 0.15 mg. of the active compound is released by a single actuation of the valve.

EXAMPLE 210

Tablets were prepared using the following components

| Active compound            | 10.00 mg.  |
|----------------------------|------------|
| Microcrystalline Cellulose | 250.00 mg. |
| Sodium Carboxymethyl Starch | 25.00 mg. |
| Magnesium Stearate         | 3.00 mg.   |
| Butylated Hydroxyanisole B.P. | 0.002 mg. |

The hydroxyanisole was dissolved in the active compound, the solution adsorbed onto the microcrystalline cellulose. This was mixed with the sodium carboxymethylcellulose and then the magnesium stearate was mixed in. Finally, the mixture was compressed to form tablets.

In the foregoing Examples 202 to 210, the liquid active compound used may, in accordance with the invention, be replaced wholly or in part by other liquid active compounds of formula I or II. If the active compound is a solid, appropriate modification will of course have to be made.

We claim:
1. An oxazole selected from the group consisting of:
2-(N-butyl-isobutyramido)-4-methyloxazole,
2-(N-butyl-hexanamido)-4-methyloxazole,
2-(N-butyl-pivalamido)-4-methyloxazole,
2-(N-butyl-isobutyramido)-4,5-dimethyloxazole,
2-(N-butyl-butyramido)-4-methyloxazole,
2-(N-hexyl-isobutyramido)-4-methyloxazole,
2-(N-butyl-iso-butyramido)-oxazole,
2-(N-butyl-pentanamido)-4-methyloxazole,
2-(N-propyl-pentanamido)-4-methyloxazole,
2-(N-butyl-phenylacetamido)-4-methyloxazole,
2-(N-cyclopentyl-pentanamido)-4-methyloxazole,
2-(N-butyl-pentanamido)-4,5-dimethyloxazole,
2-(N-butyl-butyramido)-4,5-dimethyloxazole,
2-(N-cyclohexyl-butyramido)-4-methyloxazole,
2-(N-pentyl-butyramido)-4-methyloxazole,
2-(N-propyl-hexanamido)-4-methyloxazole,
2-(N-pentyl-isobutyramido)-4-methyloxazole,
2-(N-butyl-isobutyramido-4-ethyloxazole,
2-(N-butyl-isobutyramido)-4-hydroxymethyloxazole,
2-(N-butyl-isobutyramido)-5-methyloxazole,
2-(N-cyclopentyl-isobutyramido)-4-methyloxazole,
L(+)-2-(N-butyl-2-methylbutyramido)-4-methyloxazole,
2-(N-butyl-2-methylbutyramido)-4-methyloxazole,
2-[N-(4-methoxybenzyl)-isobutyramido]-4-methyloxazole,
2-(N-butyl-cinnamamido)-4-methyloxazole,
2-(N-butyl-but-2-enamido)-4-methyloxazole, and
2-(N-butyl-isobutyramido)-5-ethyloxazole.

2. An N-substituted acylamino oxazole selected from the group consisting of
2-(N-butyl-acetamido)-4-methyloxazole,
2-(N-sec-butyl-butyramido)-4-methyloxazole,
2-(N-benzyl-propionamido)-4-methyloxazole,
2-N-butyl-propionamido)-4-methyloxazole,
2-(N-butyl-cyclobutylcarboxamido)-4-methyloxazole,
2-(N-butyl-cyclohexanecarboxamido)-4-methyloxazole,
2-(N-butyl-cyclopentane carboxamido)-4-methyloxazole,
2-(N-butyl-benzamido)-4-methyloxazole,
2-[N-butyl-(4-chlorobenzamido)]4-methyloxazole,
2-(N-butyl-acetamido)-5-acetoxymethyloxazole,
2-(N-butyl-cycloheptylcarboxamido)-4-methyloxazole,
2-(N-2-propenyl-propionamido)-4-methyloxazole,
2-(N-butyl-cyclopropylcarboxamido)-4-methyloxazole,
2-(N-butyl-isobutyramido)-5-cyclohexyloxazole,
2-(N-butyl-1-adamantylcarboxamido)-4-methyloxazole,
2-(N-allyl-butyramido)-4-methyloxazole, 2-(N-butyl-3-trifluoromethylbenzamido)-4-methyloxazole,
2-(N-butyl-3-chlorobenzamido)-4-methyloxazole,
2-[N-(2-phenylethyl)-propionamido]-4-methyloxazole
2-(N-butyl-isobutyramido)-4-isobutyryloxy methyloxazole,
2-[N-(2-methylbutyl)-butyramido]-4-methyloxazole,
2-[N-(2-methylbutyl)-propionamido]-4-methyloxazole,
2-[N-(2-methylbutyl)-isobutyramido]-4-methyloxazole,
2-(N-butyl-4-fluorobenzamido)-4-methyloxazole,
2-(N-pentyl-propionamido)-4-methyloxazole,
2-(N-hexyl-propionamido)-4-methyloxazole,
2-(N-butyl-chloroacetamido)-4-methyloxazole,
2-(N-butyl-isobutyramido)-4-methyl-5-hydroxyoxazole,
1-2-(N-sec-butyl-butyramido)-4-methyloxazole,
d-2-(N-sec-butyl-butyramido)-4-methyloxazole,
2-(N-butyl-isobutyramido)-4-formyloxazole,
2-(N-butyl-4-chlorobutyramido)-4-methyloxazole,
2-(N-2-propynyl-isobutyramido)-4-methyloxazole,
2-[N-(3-methylbenzyl)-isobutyramido]-4-methyloxazole,
5-(N-butyl-trifluoroacetamido)-2-methyloxazole,
2-[N-(3-carboxypropyl)-octanamido]-4-methyloxazole,
2-[N-(3-chloropropyl)-pentanamido]-4-methyloxazole,
2-[N-(3-chloropropyl)-isobutyramido]-4-methyloxazole, and
5-(N-methyl-acetamido)-4-methyl-2-phenyloxazole.

3. A pharmaceutical formulation useful for treating asthma in animals comprising an amount sufficient to treat asthma of an oxazole of claim 1 in association with a pharmaceutically acceptable carrier therefor.

4. A pharmaceutical formulation useful for treating asthma in animals comprising an amount sufficient to treat such asthma of an oxazole of claim 2 in association with a pharmaceutically acceptable carrier therefor.

5. A method of treating an animal suffering from asthma which comprises administering to such animal an amount effective for treating asthma of an oxazole of claim 1.

6. A method of treating an animal suffering from asthma which comprises administering to such animal an amount effective for treating asthma of an oxazole of claim 2.

7. An oxazole according to the formula

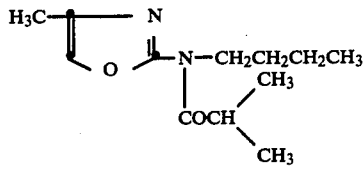

8. A pharmaceutical formulation useful for treating asthma in animals comprising a therapeutically effective amount of 2-(N-butyl-isobutyramido)-4-methyloxazole in association with a pharmaceutically acceptable carrier therefor.

9. A method of treating an animal suffering from asthma which comprises administering to such animal an amount effective for treating asthma of 2-(N-butyl-isobutyramido)-4-methyloxazole.

* * * * *